(12) United States Patent
Nakamura et al.

(10) Patent No.: US 6,316,390 B1
(45) Date of Patent: Nov. 13, 2001

(54) TRIKETONE DERIVATIVES

(75) Inventors: Kazufumi Nakamura; Mitsuru Shibata; Kazuyoshi Koike, all of Chiba-ken (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 0 days.

(21) Appl. No.: 09/581,231

(22) PCT Filed: Dec. 24, 1997

(86) PCT No.: PCT/JP97/04797

§ 371 Date: Jun. 23, 2000

§ 102(e) Date: Jun. 23, 2000

(87) PCT Pub. No.: WO99/33820

PCT Pub. Date: Aug. 7, 1999

(51) Int. Cl.[7] ............................ A01N 43/18; C07D 335/06
(52) U.S. Cl. ............................................. 504/288; 549/23
(58) Field of Search ................................ 504/288; 549/23

(56) References Cited

U.S. PATENT DOCUMENTS

| | | | |
|---|---|---|---|
| 5,468,878 | * 11/1995 | Nasuno et al. | 549/23 |
| 5,480,858 | * 1/1996 | Sakamoto et al. | 504/288 |
| 5,607,898 | 3/1997 | Nakamura et al. | |
| 5,801,121 | * 9/1998 | Kamano et al. | 504/288 |
| 5,990,049 | * 11/1999 | Nakamura et al. | 504/288 |
| 6,103,668 | 8/2000 | Nakamura et al. | |

FOREIGN PATENT DOCUMENTS

| | | |
|---|---|---|
| WO 97/03064 | 1/1997 | (WO) . |
| WO 97/08164 | 3/1997 | (WO) . |

* cited by examiner

Primary Examiner—Deborah C. Lambkin
(74) Attorney, Agent, or Firm—Oblon, Spivak, McClelland, Maier & Neustadt, P.C.

(57) ABSTRACT

A triketone derivative represented by the following formula or a salt thereof:

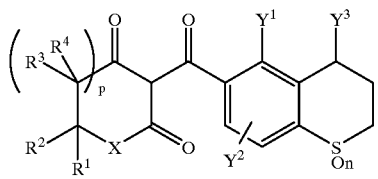

wherein, $Y^1$, $Y^2$, $Y^3$, n, p, $R^1$, $R^2$, $R^3$, $R^4$ and X are as defined in claims, prevents growth of a wide variety of cropland weeds in small application rates without causing injury to crops.

6 Claims, No Drawings

TRIKETONE DERIVATIVES

This Appln is a 371 of PCT/JP97/04797 Dec. 24, 1997.

TECHNICAL FIELD

The present invention relates to triketone derivatives including their salts and herbicidal compositions containing the derivatives. More particularly, the present invention relates to triketone derivatives having specific structure and their salts, and herbicidal compositions containing the derivatives as effective component which show a broad spectrum of controlling growth of cropland weeds even in small application rates without causing injury to field crops such as corn, etc.

BACKGROUND ART

Since herbicides are chemicals important for saving weed control working and achieving high crop yield, research and development of new herbicides have been extensively conducted for a long time and numerous types of chemicals have been practically used. However, the need still continues for new chemicals having more effective weed control activity, particularly, new chemicals which can selectively control the growth of objective weeds in small application rates without causing injury to agronomic crops.

In croplands of corn, etc., triazine herbicides such as atrazine and acid anilide herbicides such as alachlor and metolachlor have been used. However, atrazine is not sufficient for controlling Graminaceous weeds, although effective for controlling broad-leaved weeds. Alachlor and metolachlor in turn exhibit a low controlling activity against active broad-leaved weeds, although effective for controlling Graminaceous weeds. No herbicide is found at present, which can control the growth of gramineous weeds and broad-leaved weeds simultaneously by sole application. Moreover, the above herbicides must be used in larger amounts and not environmentally suitable.

Under the above circumstances, the inventors developed and proposed novel triketone derivatives having thiochroman ring (WO97/03064), which is represented by the following compound.

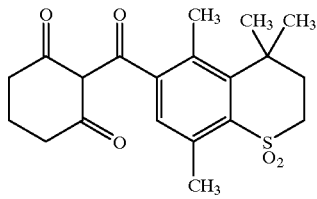

WO97/08164 discloses structurally specific triketone derivatives having thiochroman ring, which are represented by the following compounds.

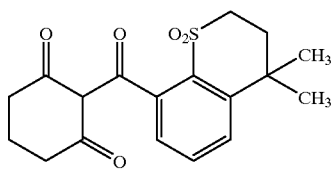

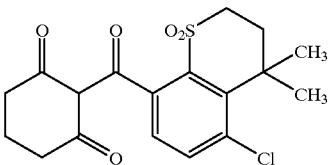

However, the proposed compounds are still insufficient in herbicidal activity particularly in foliage treatment of Graminaceous weeds.

MEANS FOR SOLVING THE PROBLEMS

Therefore, objects of the present invention are to provide novel triketone derivatives having a broad spectrum of controlling the growth of cropland weeds in small application rates without causing injury to crops such as corn, and herbicidal compositions containing them.

As the result of extensive studies to achieve the above objects, the inventors have found that novel triketone derivatives represented by the formula (I) or their salts prevent growth of various cropland weeds in small application rates without causing injury to crops such as corn. The present invention has been accomplished based on this finding.

Thus, a first object of the present invention is achieved by a triketone derivative represented by the following formula (I) or a salt thereof:

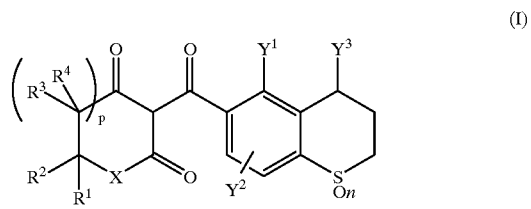

(I)

wherein
$Y^1$ represents $C_1$–$C_4$ alkyl, halogen or $C_1$–$C_4$ haloalkyl;
$Y^2$ represents hydrogen, $C_1$–$C_4$ alkyl or halogen;
$Y^3$ represents hydrogen or $C_1$–$C_6$ alkyl;
n represents 0, 1 or 2;
p represents 0 or 1;
$R^1$, $R^2$, $R^3$ and $R^4$ each independently represents hydrogen, $C_1$–$C_4$ alkyl or phenyl, $R^1$ or $R^2$ being optionally bonded to $R^3$ or $R^4$ to form a double bond in the molecule when p is 1; and
X represents oxygen group atom or group represented by the following formula:

wherein $R^5$ and $R^6$ each independently represents hydrogen, $C_1$–$C_4$ alkyl or phenyl. Hereinafter, the triketone derivatives and salts thereof may be collectively referred to as "triketone derivatives".

A second object of the present invention is achieved by herbicidal composition containing the tiiketone derivatives represented by the formula (I) and/or salts thereof as effective components.

PREFERRED EMBODIMENT TO CARRY OUT THE INVENTION

The triketone derivatives of the present invention will be described first.

The triketone derivatives of the present invention are represented by the formula (I).

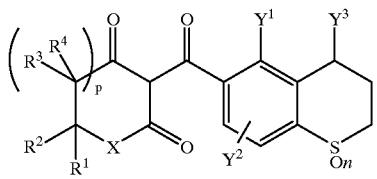

(I)

In the formula (I), $Y^1$ represents $C_1$–$C_4$ alkyl, halogen or $C_1$–$C_4$ haloalkyl. Examples of $C_1$–$C_4$ alkyl include methyl, ethyl, propyls such as n-propyl and i-propyl and butyls such as n-butyl and i-butyl. Examples of halogen include fluorine, chlorine, bromine and iodine. Examples of $C_1$–$C_4$ haloalkyl include the above alkyls substituted with 1 to 9 halogen atoms such as —$CH_2Cl$, —$CHCl_2$, —$CCl_3$, —$CH_2F$, —$CHF_2$, —$CF_3$, —$CCl_2CH_3$, —$CF_2CH_3$, —$CH_2CH_2F$, —$CH_2CH_2CHF_2$, —$CF_2CF_3$, —$CH_2CH_2CHCl_2$, —$CH_2CH_2CH_2CH_2Cl$, —$CH_2CH_2CH_2CH_2F$, —$CH(CH_3)CH_2Cl$, —$CH(CH_3)CH_2F$ and —$CH(C_2H_5)CH_2F$. Among these substituents, methyl, chlorine and —$CF_3$ are preferable, and methyl is more preferable as $Y^1$.

$Y^2$ represents hydrogen, $C_1$–$C_4$ alkyl or halogen. Examples of $C_1$–$C_4$ alkyl and halogen are the same as those for $Y^1$. $Y^2$ is preferably hydrogen, methyl or fluorine and more preferably hydrogen or methyl. $Y^2$ representing $C_1$–$C_4$ alkyl or halogen may be bonded to either 7-position or 8-position, preferably 8-position of the thiochroman ring.

$Y^3$ represents hydrogen or $C_1$–$C_6$ alkyl. Examples of $C_1$–$C_6$ alkyl include methyl, ethyl, propyls such as n-propyl and i-propyl, butyls such as n-butyl and i-butyl, pentyls such as n-pentyl and hexyls such as n-hexyl. Hydrogen, methyl or ethyl is preferable as $Y^3$.

Subscript "n" represents the number of oxygen bonded to sulfur atom, and is 0, 1 or 2. Sulfur constitutes sulfide when n is 0, sulfoxide when n is 1, and sulfone when n is 2. The subscript n is preferably 2, i.e., sulfone is preferable.

Subscript "p" represents 0 or 1. (Hetero)cyclic diketone ring bonded to the thiochroman ring is a five-membered ring when p is 0 and a six-membered ring when p is 1. The subscript p is preferably 1, i.e., the (hetero)cyclic diketone ring bonded to the thiochroman ring is preferably six-membered ring.

$R^1$, $R^2$, $R^3$ and $R^4$ each independently represents hydrogen, $C_1$–$C_4$ alkyl or phenyl. Examples of $C_1$–$C_4$ alkyl are the same as those for $Y^1$. When p is 1, $R^1$ or $R^2$ may be bonded to $R^3$ or $R^4$ to form a double bond in the molecule. $R^1$, $R^2$, $R^3$ and $R^4$ each is preferably hydrogen or methyl and more preferably hydrogen.

X represents oxygen group atom or group represented by the following formula:

Examples of oxygen group atom include oxygen and sulfur. $R^5$ and $R^6$ in the alkylidene group represented by the above formula each independently represents hydrogen, $C_1$–$C_4$ alkyl or phenyl. Examples of $C_1$–$C_4$ alkyl are the same as those for $Y^1$. X is preferably oxygen or a group represented by the following formula:

wherein $R^5$ and $R^6$ each independently represents hydrogen or methyl.

The triketone derivatives represented by the formula (I) may be tautomerized as shown below. The following tautomers are included in the ketone derivatives of the present invention.

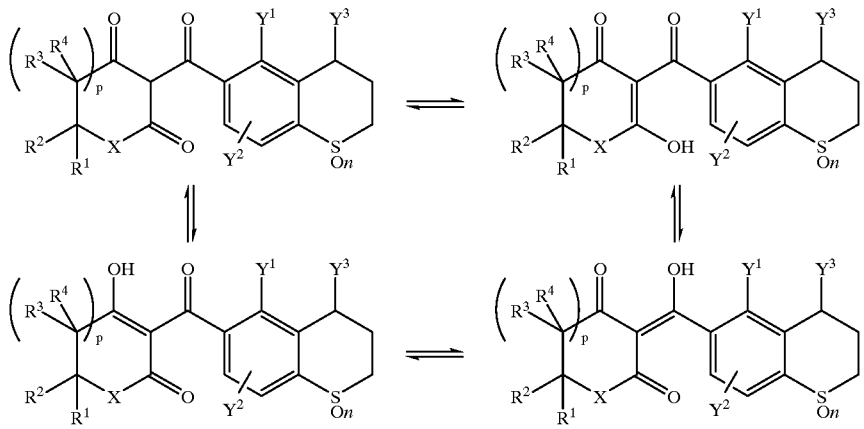

In the above formulae, $Y^1$, $Y^2$, $Y^3$, n, p, $R^1$, $R^2$, $R^3$, $R^4$ and X are as defined in the formula (I).

The triketone derivatives represented by the formula (I) are acidic substances and can be easily made into salts by treating with a base. The salts thus formed are also included in the present invention.

Known bases can be used without specific restriction. Examples of the base include organic bases such as amines and anilines and inorganic bases such as sodium compounds and potassium compounds. Examples of the amines include monoalkylamines, dialkylamines and trialkylamines. Alkyl in the alkylamines is generally $C_1$–$C_4$ alkyl. Examples of the anilines include aniline, monoalkylanilines and dialkylanilines. Alkyl in the alkylanilines is generally $C_1$–$C_4$ alkyl. Examples of the sodium compounds include sodium hydroxide and sodium carbonate. Examples of the potassium compounds include potassium hydroxide and potassium carbonate. Of the above bases, sodium compounds, potassium compounds and trialkylamines are preferable.

The triketone derivatives of the present invention can be produced, for example, by the following process.

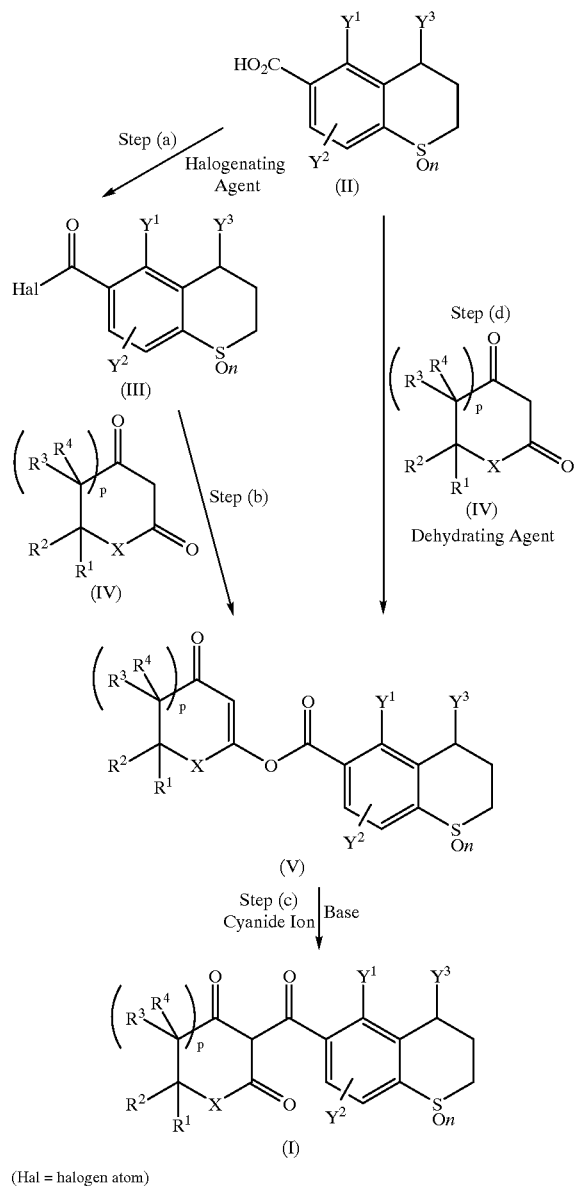

(Hal = halogen atom)

In the above formulae, $Y^1$, $Y^2$, $Y^3$, n, p, $R^1$, $R^2$, $R^3$, $R^4$ and X are as defined in the formula (I).

A compound represented by the formula (II) is reacted with a halogenating agent to prepare a compound represented by the formula (III), which is then reacted with a compound represented by the formula (IV) to prepare a compound represented by the formula (V). Then, the compound (V) is rearranged into the triketone derivatives represented by the formula (I). The compound (V) may be also prepared by the reaction of the compound (II) with the compound (IV) in the presence of a dehydrating agent such as dicyclohexylcarbodiimide (hereinafter abbreviated as DCC).

Each step of the process will be described specifically below.

Step (a)

In the step (a), the compound (II) is reacted with a halogenating agent to form the compound (III). As the halogenating agent, for example, thionyl chloride, phosphorus oxychloride, etc. can be used. The halogenating agent is generally used in equimolecular amount or more to the compound (II). The reaction may be conducted in the presence or absence of a solvent. The solvent usable in the reaction is not particularly limited and may be inert solvent such as 1,2-dichloroethane and chloroform. An excess amount of thionyl chloride as the halogenating agent also serves as the solvent. The reaction temperature of the step (a) is not particularly limited, and preferably from 0° C. to the refluxing temperature of the reaction system or the boiling point of the solvent and more preferably 60° C. or its vicinity.

Step (b)

In the step (b), the compound (III) obtained by the step (a) is reacted with the compound (IV) to form the compound (V). The compound (III) and the compound (IV) are reacted by mixing in a molar ratio of 1:1 to 1:3 generally in the presence of a solvent inert to the reaction. Examples of the solvent inert to the reaction include dioxane, acetonitrile, benzene, toluene, chloroform, methylene chloride and 1,2-dichloroethane. Two-phase solvents such as water-benzene, water-toluene and water-chloroform can be also used. To make the reaction proceed smoothly, a base such as sodium hydroxide, potassium hydroxide, sodium carbonate, potassium carbonate, triethylamine and pyridine may be used in equimolecular amount or more to the compound (III). The reaction temperature of the step (b) is not particularly limited, and preferably 0 to 60° C., more preferably 0° C. to room temperature.

Step (c)

In the step (c), the compound (V) obtained in the step (b) is rearranged into the triketone derivative represented by formula (I). The step (c) is conducted preferably in the presence of a solvent inert to the reaction such as methylene chloride, 1,2-dichloroethane, toluene, acetonitrile, N,N-dimethylformamide and ethyl acetate. Acetonitrile is preferred. In the step (c), a base such as sodium carbonate, potassium carbonate, triethylamine and pyridine is added 1 to 4 times, preferably 1 to 2 times the equivalent amount to the compound (V). The step (c) is preferably carried out in the presence of hydrogen cyanide or a compound capable of generating cyanide anion in the reaction system, i.e., so called cyanide source so as to make the reaction proceed catalytically and smoothly. Examples of the cyanide source include metal cyanides such as sodium cyanide and potassium cyanide and cyanohydrin compounds of lower alkyl ketones, for example, cyanohydrins of about $C_3$–$C_5$ alkyl ketones such as acetone cyanohydrin and methyl isopropyl ketone cyanohydrin. When a metal cyanide is used, it is preferred to add a phase-transfer catalyst such as crown ethers to the reaction system so as to proceed the reaction more smoothly. Hydrogen cyanide or the cyanide source is used generally 0.01 to 0.5 molar equivalent, preferably 0.05 to 0.2 molar equivalent to the compound (V). The reaction temperature of the step (c) is not particularly limited, and is generally 0 to 80° C., preferably 20 to 40° C.

Step (d)

The compound (V) can be obtained also by the step (d). In the step (d), the condensation reaction of the compound (II) and the compound (IV) is conducted in the presence of a solvent and a dehydrating agent such as DCC, thereby forming the compound (V). The solvent used for the condensation reaction is not particularly limited as long as the solvent is inert to the reaction. In general, acetonitrile or tert-amyl alcohol is preferably used. The reaction temperature of the step (d) is not particularly limited as long as within the range of 0° C. to the boiling point of the solvent, and is preferably around room temperature. Usable dehydrating agents other than DCC may be 1,1-carbonyldiimidazole (CDI) and 1-(3-dimethylaminopropyl)-3-ethylcarbodiimide (EDC). The dehydrating agent is used in 1.0 to 3.0 equivalent and preferably 1.0 to 1.5 equivalent to the compound (II). The compound (II) and the compound (IV) are mixed in a molar ratio (compound (II)/compound (IV)) of 1:1 to 1:3 and preferably 1:1 to 1:1.5. The condensation reaction is completed generally in about 8 hours. However, the reaction time can be suitably selected from 1 to 48 hours, preferably from 5 to 15 hours depending on kinds of the compounds (II) and (V).

The compound (V) obtained by the steps (a) and (b) or the step (d) is treated in the following step (c) generally after being isolated. However, the compound (V) may be treated without isolation.

The compound (II) which is used as the starting material in the production of the triketone derivatives of the present invention can be prepared by the method described in U.S. Pat. No. 5,607,898 or similar methods. The compounds of the formula (IV) are mostly known or easily produced by known methods.

Preferred triketone derivatives (I) of the present invention are listed in Table 1.

As the solvent serving as the liquid carrier, organic solvents are generally used. Specifically, the solvent may be aromatic hydrocarbons such as benzene, toluene and xylene; chlorinated hydrocarbons such as o-chlorotoluene, trichloroethane and trichloroethylene; alcohols such as cyclohexanol, amyl alcohol and ethylene glycol; ketones such as isophorone, cyclohexanone and cyclohexenylcyclohexane; ethers such as butylcellosolve, diethyl ether and methyl ethyl ether; esters such as isopropyl acetate, benzyl acetate and methyl phthalate; amides such as dimethylformamide; and mixtures thereof.

The fine powder of minerals are used as the solid carrier, which may be powders of oxides such as diatomaceous earth and slaked lime; powders of phosphates such as apatite; powders of sulfates such as gypsum and powders of silicates such as talc, pyroferrite, clay, kaolin, bentnite, acidic white clay, white carbon, quartz and silica.

As the surfactant, usable are any of anionic surfactants such as alkyl sulfates, alkylbenzenesulfonates, dialkyl sulfosuccinates and condensates of naphthalenesulfonic acid and form aldehyde; nonionic surfactants such as polyoxyethylene alkyl ethers, polyoxyethylene alkylphenol ethers, polyoxyethylene alkylamines and sorbitan esters of fatty acids; cationic surfactants such as alkylamine salts of fatty acids and quaternary ammonium salts; and amphoteric surfactants such as amino acids and betaine.

Herbicidal compositions of wettable powder formulation can be prepared, in general, by blending 10 to 55% by

TABLE 1

(I)

$$\left(R^3 \overset{R^4}{\underset{R^1}{\bigvee}}_p \overset{O}{\underset{X}{\bigvee}} \overset{O}{\underset{O}{\bigvee}} \overset{Y^1}{\underset{Y^2}{\bigvee}} \overset{Y^3}{\underset{On}{\bigvee}} \right) \quad \left( \begin{array}{l} R^1 = R^2 = R^3 = R^4 = H \\ p = 1 \\ X = CR^5R^6 \\ R_5 = R_6 = H \\ n = 2 \end{array} \right)$$

| Compound No. | $Y^1$ | $Y^2$ | $Y^3$ |
|---|---|---|---|
| 1 | $CH_3$ | H | H |
| 2 | $CH_3$ | 8-$CH_3$ | H |
| 3 | $CH_3$ | 8-$CH_3$ | $CH_3$ |
| 4 | $CH_3$ | 8-$CH_3$ | $CH_2CH_3$ |
| 5 | $CH_3$ | 8-$CH_3$ | $CH_2CH_2CH_3$ |
| 6 | $CH_3$ | 8-$CH_3$ | $CH_2CH_2CH_2CH_3$ |
| 7 | $CH_3$ | 8-$CH_3$ | $CH_2CH_2(CH_3)_2$ |
| 8 | Cl | H | H |
| 9 | Cl | H | $CH_3$ |
| 10 | Cl | H | $CH_2CH_3$ |
| 11 | Cl | 8-$CH_3$ | H |
| 12 | Cl | 8-$CH_3$ | $CH_3$ |
| 13 | Cl | 8-$CH_3$ | $CH_2CH_3$ |

In Table 1, "8-$CH_3$" in the column entitled $Y^2$ means that methyl is attached to 8-position of the thiochroman ring.

Next, the herbicidal compositions containing the triketone derivatives of the present invention will be described.

The herbicidal compositions of the present invention contain the triketone derivatives of the formula (I) and/or salts thereof as the effective component. The triketone derivatives are mixed with a liquid carrier such as solvent or a solid carrier such as fine mineral powder to prepare formulations such as wettable powders, emulsifiable concentrates, dusts and granules. A surfactant is preferably added to improve emulsifying property, dispersing property and spreading property during the mixing of the triketone derivatives and the carrier.

weight of triketone derivative, 40 to 88% by weight of solid carrier and 2 to 5% by weight of surfactant. Emulsifiable concentrates can be prepared, in general, by mixing 20 to 50% by weight of triketone derivative, 35 to 75% by weight of solvent and 5 to 15% by weight of surfactant. Dusts can be prepared, in general, by blending 1 to 15% by weight of triketone derivative, 80 to 97% by weight of solid carrier and 2 to 5% by weight of surfactant. Granules can be prepared, in general, by blending 1 to 15% by weight of triketone derivative, 80 to 97% by weight of solid carrier and 2 to 5% by weight of surfactant.

In addition to the triketone derivatives of the formula (I), the herbicidal compositions of the present invention may further contain, if necessary, another herbicidally active component known in the art, which may suitably selected from phenoxy herbicides, diphenyl ether herbicides, triazine herbicides, urea herbicides, carbamate herbicides, thiol carbamate herbicides, acid anilide herbicides, pyrazole herbicides, phosphoric acid herbicides, sulfonylurea herbicides and oxadiazine herbicides.

The herbicidal compositions of the present invention may further contain, if necessary, insecticide, antibiotic, plant growth regulator and fertilizer.

The present invention will be described more specifically with reference to the following Preparation Examples and Herbicidal Examples. However, the present invention is not intended to be limited thereto.

PREPARATION EXAMPLE 1

Synthesis of 6-(1,3-dioxycyclohexan-2-yl)-5-methylthiochroman 1,1-dioxide (Compound No. 1)

Into a suspension of 0.80 g (3.3 mmol) of 5-methylthiochroman-6-carboxylic acid 1,1-dioxide in 4 ml of 1,2-dichloroethane, 0.29 ml (1.2 eq, 4.0 mmol) of thionyl chloride was added and heated for one hour and 30 minutes under refluxing. Excess thionyl chloride and 1,2-dichloroethane were evaporated off under reduced pressure, followed by addition of 1.6 ml acetonitrile. After cooling the resultant mixture in ice water bath, a solution prepared by dissolving 0.44 g (1.2 eq, 3.9 mmol) of 1,3-cyclohexanedione and 0.55 ml (1.2 eq, 3.9 mmol) of triethylamine in 2.4 ml of acetonitrile was added dropwise to the mixture, which was then stirred for 30 minutes in the ice water bath and further stirred for two hours while allowing the temperature to return to room temperature. Then, 0.55 ml (1.2 eq, 3.9 mmol) of triethylamine and 0.10 ml (0.33 eq, 1.1 mmol) of acetone cyanohydrin were added to the reaction solution, followed by stirring for three hours at 40° C. After evaporating off acetonitrile under reduced pressure, ice water and 10 ml of aqueous 10% sodium hydroxide were added to the mixture, which was then washed with methylene chloride. After adding 20 ml of concentrated hydrochloric acid, the reaction solution was extracted with methylene chloride twice and dried over anhydrous sodium sulfate. After evaporating off the solvent under reduced pressure, 0.88 g (79% yield) of 6-(1,3-dioxycyclohexan-2-yl)-5-methylthiochroman 1,1-dioxide was obtained. The results of $^1$H-NMR (nuclear magnetic resonance) analysis and IR (infrared) analysis are shown below:

$^1$H-NMR (CDCl$_3$): 1.9–3.1 (m, 10H), 2.14 (s, 3H), 3.2–3.5 (m, 2H), 7.08 (d, 1H), 7.82 (d, 1H)

IR (KBr): 3500, 2990, 1690, 1550, 1300, 1135 cm$^{-1}$

PREPARATION EXAMPLES 2 to 13

Synthesis of Compounds Nos. 2 to 13

In the same manner as in Preparation Example 1 except that the corresponding carboxylic acids were used in place of 5-methylthiochroman-6-carboxylic acid 1,1-dixode, Compounds Nos. 2 to 13 were obtained. The results of $^1$H-NMR analysis and IR analysis are shown in Table 2.

TABLE 2

| Compound No. | $^1$H-NMR (ppm) Internal Standard: tetrahydrofuran Solvent: heavy chloroform, (a): heavy acetone | IR (cm$^{-1}$) KBr tablet method |
|---|---|---|
| 2 | 2.0–3.0(m, 10H), 2.08(s, 3H), 2.71(s, 3H), 3.3–3.5(m, 2H), 6.84(s, 1H) | 3450, 2950, 1680, 1560, 1295, 1125 |
| 3 | 1.33(d, 3H), 1.9–2.9(m, 8H), 2.17(s, 3H), 2.70(s, 3H), 3.2–3.9(m, 3H), 6.83(s, 1H) | 3450, 2970, 1675, 1550, 1280, 1115 |
| 4 | 1.04(t, 3H), 1.1–3.8(m, 13H), 2.15(s, 3H), 2.70(s, 3H), 6.82(s, 1H) | 3450, 2950, 1675, 1540, 1280, 1105 |
| 5 | 0.9–3.9(m, 18H), 2.16(s, 3H), 2.70(s, 3H), 6.81(s, 1H) | 3550, 2975, 1685, 1565, 1290, 1120 |
| 6 | 0.8–3.9(m, 20H), 2.15(s, 3H), 2.69(s, 3H), 6.81(s, 1H) | 3550, 2950, 1680, 1570, 1295, 1120 |
| 7 | 0.99(d, 3H), 1.05(d, 3H), 1.2–3.1(m, 11H), 2.19(s, 3H), 2.64(s, 3H), 3.2–3.8(m, 3H), 6.92(s, 1H)$^{(a)}$ | 3450, 2980, 1690, 1565, 1300, 1130 |
| 8 | 1.8–3.2(m, 10H), 3.3–3.5(m, 2H), 7.22(d, 1H), 7.83(d, 1H) | 3500, 2955, 1680, 1560, 1315, 1145 |
| 9 | 1.41(d, 3H), 2.1–4.0(m, 11H), 7.34(d, 1H), 7.84(d, 1H)$^{(a)}$ | 3450, 2950, 1680, 1575, 1300, 1135 |
| 10 | 1.09(t, 3H), 1.2–3.9(m, 13H), 7.34(d, 1H), 7.84(d, 1H) | 3500, 2995, 1685, 1575, 1300, 1140 |
| 11 | 2.0–3.2(m, 10H), 2.73(s, 3H), 3.3–3.5(m, 2H), 6.96(s, 1H) | 3490, 2960, 1685, 1565, 1300, 1150 |
| 12 | 1.40(d, 3H), 1.9–3.1(m, 8H), 2.73(s, 3H), 3.2–4.0(m, 3H), 6.95(s, 1H) | 3450, 2950, 1680, 1570, 1305, 1125 |
| 13 | 1.05(t, 3H), 1.2–2.8(m, 10H), 2.65(s, 3H), 3.1–3.9(m, 3H), 7.04(s, 1H)$^{(a)}$ | 3500, 2950, 1680, 1590, 1290, 1130 |

(1) Preparation of Herbicidal Compositions

A mixture consisting of 97 parts by weight of talc (Zeaklite, trade name of Zeaklite Kogyo Co., Ltd.) as a carrier, 1.5 parts by weight of a salt of alkylarylsulfonic acid (Neoperex, trade name of Kao Atlas Co., Ltd.) as a surfactant and 1.5 parts by weight of a nonionic surfactant and an anionic surfactant (Solpol 800A, trade name of Toho Kagaku Kogyo Co., Ltd.) was pulverized and mixed uniformly to obtain a carrier for wettable powder.

Each herbicidal composition was prepared by pulverizing and uniformly mixing 90 parts by weight of the carrier for wettable powder and 10 parts by weight of the compound of the present invention. In the same manner, a herbicidal composition was prepared as Comparative Example 1 using the following compound (A).

Compound (A): Compound Disclosed in WO97/03064

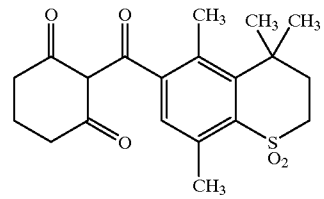

(2) Ratings for Herbicidal Effect and Injury to Crops

The herbicidal effect and the injury to crops were evaluated by the following ratings obtained by residual plant ratios defined by the following equation:

Residual plant ratio=(Residual weight in treated plot/Residual weight in untreated plot)×100

Ratings

| | Residual plant ratio (%) |
|---|---|
| Herbicidal effect | |
| 0 | 81 to 100 |
| 1 | 61 to 80 |
| 2 | 41 to 60 |
| 3 | 21 to 40 |
| 4 | 1 to 20 |
| 5 | 0 |
| Damages on crops | |
| − | 100 |
| ± | 95 to 99 |
| + | 90 to 94 |
| ++ | 80 to 89 |
| +++ | 0 to 79 |

(3) Biological Test (Foliage Treatment in Cropland; Herbicidal Examples 1 to 13 and Herbicidal Comparative Example A)

Seeds of *Xanthium strumarium, Ahutilon theophrasti, Chenopodium album, Ambrosia artemisiaefolia, Digitaria adscendens* and *Setaria viridis* and corn were sowed onto cropland soil in respective Wagner pots of 1/5000 are and covered with soil. The pots were maintained in a greenhouse for germination. When the plants had grown to three to four leaf stage, a water dispersion containing an amount of each herbicidal composition prepared in (1) was uniformly sprayed to the foliage of each plant in a rate of 2000 liter/ha. Treated plants and untreated controls were maintained in a greenhouse for 30 days, after which the herbicidal effect and injury to crops were evaluated based on the ratings mentioned in (2). The results are shown in Table 3.

TABLE 3

(foliage treatment)

| Example No. | Application Rate (g/ha) | Herbicidal Effect | | | | | | Injury to Crops corn |
|---|---|---|---|---|---|---|---|---|
| | | (a) | (b) | (c) | (d) | (e) | (f) | |
| 1 | 160 | 5 | 5 | 5 | 5 | 4 | 4 | — |
| 2 | 160 | 4 | 5 | 5 | 5 | 4 | 4 | — |
| 3 | 160 | 5 | 5 | 5 | 5 | 4 | 4 | — |
| 4 | 160 | 5 | 5 | 5 | 5 | 5 | 5 | — |
| 5 | 160 | 5 | 5 | 5 | 5 | 5 | 4 | — |
| 6 | 160 | 4 | 4 | 4 | 4 | 4 | 4 | — |
| 7 | 160 | 5 | 5 | 5 | 5 | 5 | 5 | — |
| 8 | 160 | 5 | 5 | 5 | 5 | 5 | 4 | — |
| 9 | 160 | 4 | 5 | 5 | 5 | 4 | 4 | — |
| 10 | 160 | 4 | 5 | 5 | 5 | 4 | 4 | — |
| 11 | 160 | 4 | 5 | 5 | 5 | 4 | 4 | — |
| 12 | 160 | 4 | 4 | 4 | 4 | 4 | 4 | — |
| 13 | 160 | 5 | 5 | 5 | 5 | 4 | 4 | — |
| A | 160 | 5 | 5 | 5 | 5 | 1 | 1 | — |

(a) *Xanthium strumarium*
(b) *Abutilon theophrasti*
(c) *Chenopodium album*
(d) *Ambrosia artemisiaefolia*
(e) *Digitaria adscendens*
(f) *Setaria viridis*

The results in Table 3 show that the herbicidal compositions of the present invention prevent growth of various weeds in cropland by small application rates without causing any injury to corn. In contrast, the compound (A) exhibits inferior effects in preventing growth of Graminaceous weeds such as *Digitaria adscendens* and *Setaria viridis*.

What is claimed is:

1. A triketone derivative represented by the following formula or a salt thereof:

wherein $Y^1$ represents $C_1$–$C_4$ alkyl, halogen or $C_1$–$C_4$ haloalkyl;

$Y^2$ represents hydrogen, $C_1$–$C_4$ alkyl or halogen;

$Y^3$ represents hydrogen or $C_1$–$C_6$ alkyl;

n represents 0, 1 or 2;

p represents 0 or 1;

$R^1$, $R^2$, $R^3$ and $R^4$ each independently represents hydrogen, $C_1$–$C_4$ alkyl or phenyl, $R^1$ or $R^2$ being optionally bonded to $R^3$ or $R^4$ to form a double bond in the molecule when p is 1; and X represents oxygen group atom or group represented by the following formula:

wherein $R^5$ and $R^6$ each independently represents hydrogen, $C_1$–$C_4$ alkyl or phenyl.

2. The triketone derivative or a salt thereof according to claim 1, wherein n is 2.

3. The triketone derivative or a salt thereof according to claim 1, wherein X is a group represented by the formula:

wherein $R^5$ and $R^6$ are hydrogen.

4. A herbicidal composition containing a triketone derivative and/or a salt thereof as defined in claim 1 as an effective component.

5. A herbicidal composition containing a triketone derivative and/or a salt thereof as defined in claim 2 as an effective component.

6. A herbicidal composition containing a triketone derivative and/or a salt thereof as defined in claim 3 as an effective component.

* * * * *